US008961536B2

(12) United States Patent
Nikou et al.

(10) Patent No.: US 8,961,536 B2
(45) Date of Patent: Feb. 24, 2015

(54) NAVIGATED FREEHAND SURGICAL TOOL AND KIT

(75) Inventors: Constantinos Nikou, Monroeville, PA (US); Marius Giurgi, Pittsburgh, PA (US); Jim Moody, Pittsburgh, PA (US); Benjamin McCandless, Pittsburgh, PA (US); Craig Markovitz, Pittsburgh, PA (US); Adam Hahn, Pittsburgh, PA (US); Branislav Jaramaz, Pittsburgh, PA (US)

(73) Assignee: Blue Belt Technologies, Inc., Pittsburgh, PA (US)

( * ) Notice: Subject to any disclaimer, the term of this patent is extended or adjusted under 35 U.S.C. 154(b) by 588 days.

(21) Appl. No.: 13/092,851

(22) Filed: Apr. 22, 2011

(65) Prior Publication Data

US 2011/0264107 A1    Oct. 27, 2011

Related U.S. Application Data

(60) Provisional application No. 61/342,991, filed on Apr. 22, 2010.

(51) Int. Cl.
*A61B 19/00* (2006.01)
*A61B 17/16* (2006.01)
*A61B 17/00* (2006.01)

(52) U.S. Cl.
CPC ......... *A61B 17/1633* (2013.01); *A61B 17/1622* (2013.01); *A61B 19/5244* (2013.01);
(Continued)

(58) Field of Classification Search
USPC .............................. 604/22; 606/130, 167–171
See application file for complete search history.

(56) References Cited

U.S. PATENT DOCUMENTS 6,390,982 B1    5/2002    Bova et al.
6,546,279 B1    4/2003    Bova et al.
(Continued)

FOREIGN PATENT DOCUMENTS

CN          102892352 A    1/2013
WO    WO-2011133927 A2    10/2011
(Continued)

OTHER PUBLICATIONS

"Canadian Application Serial No. N/A, Voluntary Amendment filed Oct. 22, 2012", 9 pgs.
(Continued)

*Primary Examiner* — Ashley Fishback
(74) *Attorney, Agent, or Firm* — Schwegman Lundberg & Woessner, P.A.

(57) ABSTRACT

A handpiece arrangement for a tool having a retaining member configured to receive a portion of the tool in a secure position, a guard configured to cover a portion of the tool, at least one mounting member configured to receive a portion of a tracking system and an actuator mounted to the handpiece. The actuator may be configured to control the exposure of the tool. A navigated surgery kit is also provided including a tracking system, a tool in communication with the tracking system, a platform in communication with the tracking system and the tool. The platform may have a processor, a computer readable storage medium having computer readable program code configured to selectively control shaping of an object with the tool via at least one hidden object associated with a predetermined navigated surgical operation.

15 Claims, 11 Drawing Sheets

(52) U.S. Cl.
CPC ... *A61B17/1675* (2013.01); *A61B 2017/00464* (2013.01); *A61B 2019/502* (2013.01); *A61B 2019/505* (2013.01); *A61B 2019/5255* (2013.01)
USPC .......................................................... 606/130

(56) References Cited

U.S. PATENT DOCUMENTS

| | | | |
|---|---|---|---|
| 6,780,007 B1 | 8/2004 | Coffin, Sr. | |
| 2004/0092933 A1* | 5/2004 | Shaolian et al. | 606/61 |
| 2005/0216032 A1* | 9/2005 | Hayden | 606/130 |
| 2006/0011001 A1* | 1/2006 | Showalter | 74/23 |
| 2008/0009697 A1 | 1/2008 | Haider et al. | |
| 2009/0143828 A1 | 6/2009 | Stad et al. | |

FOREIGN PATENT DOCUMENTS

| | | |
|---|---|---|
| WO | WO-2011133946 A2 | 10/2011 |
| WO | WO-2011133946 A3 | 10/2011 |

OTHER PUBLICATIONS

"International Application Serial No. PCT/US2011/033657, International Preliminary Report on Patentability mailed Nov. 1, 2012", 8 pgs.

"International Application Serial No. PCT/US2011/033657, Search Report mailed Dec. 19, 2011", 4 pgs.

"International Application Serial No. PCT/US2011/033657, Written Opinion mailed Dec. 19, 2011", 6 pgs.

"International Application Serial No. PCT/US2011/033682, International Preliminary Report on Patentability mailed Jan. 17, 2013", 7 pgs.

"International Application Serial No. PCTUS2011033682, Search Report mailed Oct. 27, 2011", 2 pgs.

"International Application Serial No. PCTUS2011033682, Written Opinion mailed Oct. 27, 2011", 5 pgs.

"Japanese Application Serial No. [Pending], Voluntary Amendment filed Dec. 26, 2012", 7 pgs.

* cited by examiner

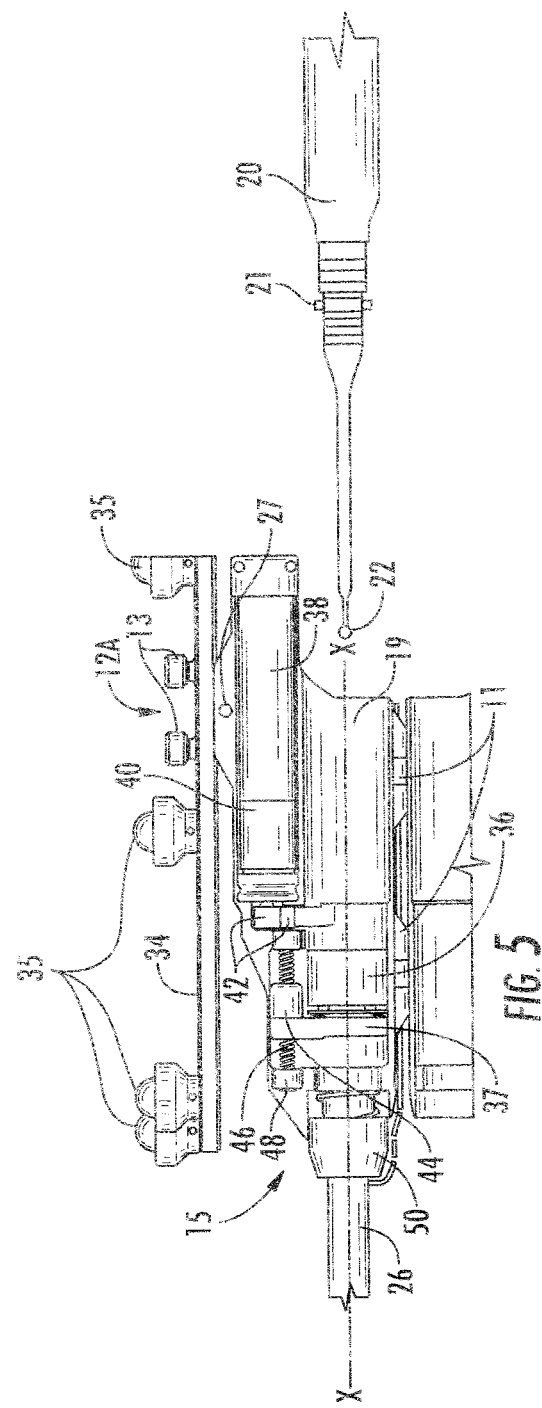

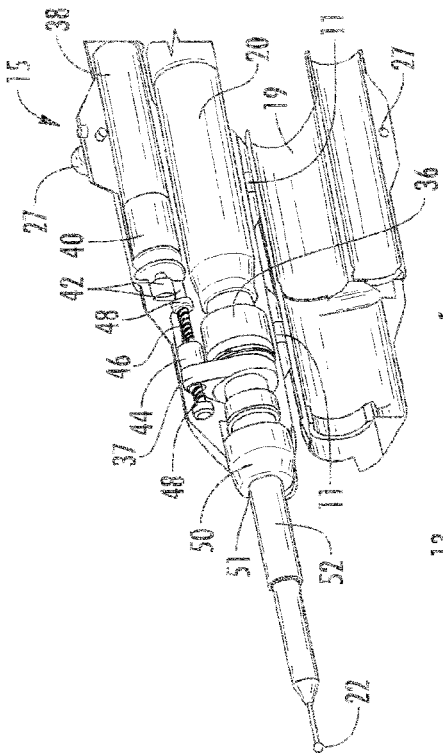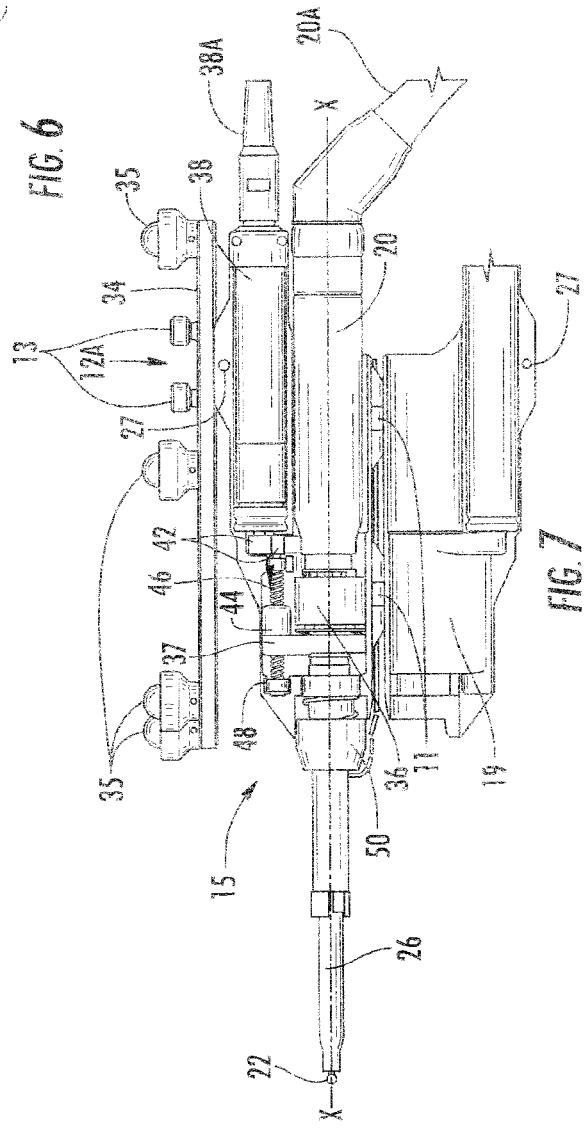

NAVIGATED FREEHAND SURGICAL TOOL AND KIT

CROSS REFERENCE TO RELATED APPLICATION

This application claims the benefit of priority of U.S. Provisional Patent Application Ser. No. 61/342,991, filed Apr. 22, 2010, on which this patent application is based and which is incorporated herein by reference in its entirety.

FIELD OF THE DISCLOSURE

The present disclosure relates generally to methods, processes, apparatus, and systems for controlling a navigated freehand surgical tool. In particular, the present invention relates to a handpiece for a navigated freehand surgical tool for use in combination with at least one of the following: a tracking system; an electronic control unit; and a software application programming interface (API) for use with a surgical navigational system.

BACKGROUND

In a bone surgery such as, for example, a total knee replacement ("TKR") procedure, it is important to carefully prepare a patient's bone to accept an implant in an anatomically correct, precise Location. Various bone cutting tools are available for use during this procedure. A navigated surgical tool may use electronic navigation to locate, fixate, adjust, and/or correct the trajectory and cutting rate of the cutting tool based on a user-defined surgical plan, while allowing the surgeon to use a freehand cutting motion.

An operative navigated surgical tool may include such elements as, for example, a cutting drill having a rotating bur to provide the cuts on the bone, for example, an inner housing into which the drill is mounted, and parts or elements comprising the electronic tracking system, computing unit(s) and software to control and monitor the operations of the cutting tool, etc.

In order to assist in the cutting of the drill, a user and/or surgeon may perform their surgery as usual using the navigation system for additional guidance and understanding of location of the drill. Other systems may be employed to fully automate the cut in the case of a robotic navigation system having a fixed target to assure a pre-determined cut.

Conventional systems may permit control methods wherein a free-hand tool can be used with navigational assistance such as described in U.S. Pat. No. 6,757,582, which is incorporated herein by reference in its entirety. A navigational system as disclosed therein, provides control for a user/surgeon by determining a distance between the cutting tool and the target shape, and robotically assisting the user/surgeon to make the desired shape on the bone.

Further a user/surgeon may wish to or may be accustomed to using specific drill(s), tracking systems, and/or navigation software for navigated surgeries. However, such user-chosen components (drill, tracking system, etc.) may not operate with or may not be used with currently available, vendor-provided navigated surgical tools. In such a case, the user may have to settle with the surgical system provided by a vendor. It is therefore desirable to provide a navigated surgical tool that can accommodate a wide variety of user-selected surgical drills and tracking systems and can also operate with navigation software, thereby giving the user/surgeon more flexibility in implementing a navigated surgical system with a desired navigated surgical tool.

SUMMARY OF INVENTION

Therefore, it is an object of the present invention to provide a handpiece that provides desirable functionality of speed and extension control, that overcome some or all of the drawbacks and deficiencies in the prior art.

In addition, it is an object of the present invention to provide such a handpiece for a navigated surgical tool that can accommodate a wide variety of user-selected surgical tools, configured to work with a handpiece, and tracking systems and can also operate with a variety of navigation software. Accordingly, the navigated freehand surgical tool kit may include a handpiece, an electronic control unit, a software API to allow a user to "build" or configure an operative navigated surgical tool wherein a user-selected surgical drill becomes configured to work with a handpiece, tracking system, and navigation software.

In one preferred and non-limiting embodiment, the present invention is directed to a handpiece arrangement for a tool having a retaining member configured to receive t least a portion of the tool in a secure position, a guard configured to cover a portion of the tool, at least one mounting member configured to receive at least a portion of a tracking system and an actuator mounted to the handpiece. The actuator may be in communication with the retaining member and is configured to move the retaining member with respect to the guard.

In another embodiment, the present invention includes a navigational surgical tool including an end effector configured to shape an object, a tracker configured to indicate the position of the end effector, and a handpiece having a first attachment portion configured to retain at least a portion of the tool and a second attachment portion configured to retain the tracker.

In another embodiment, the present invention includes a navigational surgical tool system including a surgical tool, a tracking system configured to make the location of the tool known, a handpiece configured to receive at least a portion of the tool and a guard configured to cover at least a portion of the tool. The handpiece is further configured to move the tool.

In another embodiment, the present invention includes a handpiece arrangement for a tool having a retaining member configured to receive at least a portion of the tool, a guard configured to cover at least a portion of the tool, at least one mounting member configured to receive at least a portion of a tracking system, an actuator mounted to the handpiece and configured to control the exposure of at least portion of the tool relative to the guard.

In one preferred and non-limiting embodiment, provided is a navigated surgery kit is including a tracking system, a tool in communication with the tracking system, a platform in communication with the tracking system and the tool. The platform may have a processor, a computer readable storage medium having computer readable program code configured to selectively control shaping of an object with the tool via at least one hidden object associated with a predetermined navigated surgical operation. The computer readable program code may have computer readable program code configured to: 1) selectively control shaping of an object with the tool via at least one hidden object associated with a predetermined navigated surgical operation; 2) provide at least one application programming interface object that interfaces with the hidden objects; and 3) provide at least one object template that specifies at least one task configurable for operation on the platform.

These and other features and characteristics of the present invention, as well as the methods of operation and functions of the related elements of structures and combinations of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended to unduly limit the present invention. As used in the specification and the claims, the singular form of "a", "an", and "the" include plural referents unless the context clearly dictates otherwise.

BRIEF DESCRIPTION OF DRAWINGS

FIG. 5 is a partial close-up plan view of FIG. 4 and having a drill positioned for placement within the handpiece in accordance with the present invention;

FIG. 6 is a partial perspective view of an embodiment of a handpiece in an opened position and having an exemplary tool received therein in accordance with the present invention;

FIG. 7 is a plan view of an embodiment of a handpiece in an opened position having an exemplary tool positioned therein in an extended position and with a guard attached thereto in accordance with the present invention;

DETAILED DESCRIPTION OF THE PRESENT INVENTION

Figure 1:
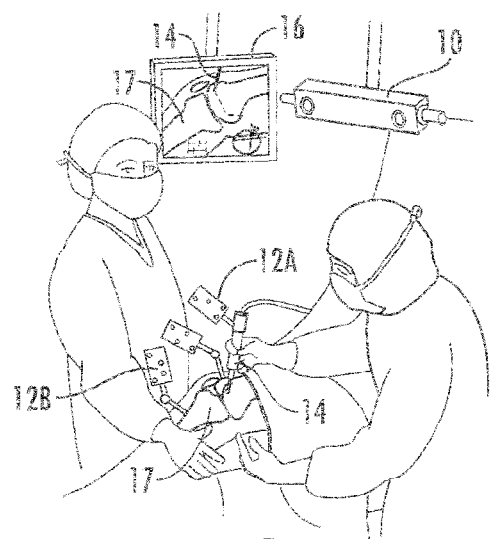
FIG. 1 is a simplified view of an exemplary optical surgical navigation setup during a standard knee replacement surgical procedure.

For purposes of the description hereinafter, the terms "upper", "lower", "right", "left", "vertical", "horizontal", "top" "bottom", "lateral" "longitudinal" and related derivatives thereof shall relate to the invention as it is oriented in the drawing figures. However, it is to be understood that the present invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as unduly limiting.

It is to be understood that the invention may assume various alternative variations and step sequences, except where expressly specified to the contrary. It is also to be understood that the specific devices and processes illustrated in the attached drawings, and described in the following specification, are simply exemplary embodiments of the invention.

Optical navigation is used in surgery to track a rigid body's location in space. FIG. 1 illustrates a simplified view of an exemplary surgical navigation setup having a tracking system such as, for example, an infrared camera 10 and a tracker 12 that may be used to perform surgical navigation. The tracker 12A may be rigidly attached to any object 14, such as a drill for example, that the user/surgeon wishes to track during the surgical procedure. The tracker 12A may comprise a unique configuration of markers 35 such as infrared reflective markers, for example. The camera 10 takes continuous pictures of the workspace during the surgical procedure, and the markers 35 may then be detected from those pictures.

Other position tracking systems may be used within the spirit and scope of the invention including, but not limited to, electromagnetic, inertial, hybrid, etc. Using the known rigid spatial relationship of the markers 35 on the image frame obtained by the camera 10, the position (i.e., the location and orientation) of the object 14 in a 3D (three dimensional) space can be determined. The location of the object 14 can be continuously output to a computer program that can integrate this location with patient anatomy positional information that may be obtained from a CT scan or ultrasound image, for example, thus permitting a determination of the location and orientation of the object 14 with respect to a remainder or reference potion of the patient anatomy. The location and orientation of object 14 relative to the patient anatomy, such as bone 17, also can be continuously displayed on a display terminal or monitor 16. Thus, the user/surgeon will be able to know and understand the location of the object 14 relative to the bone 17.

Figure 2:
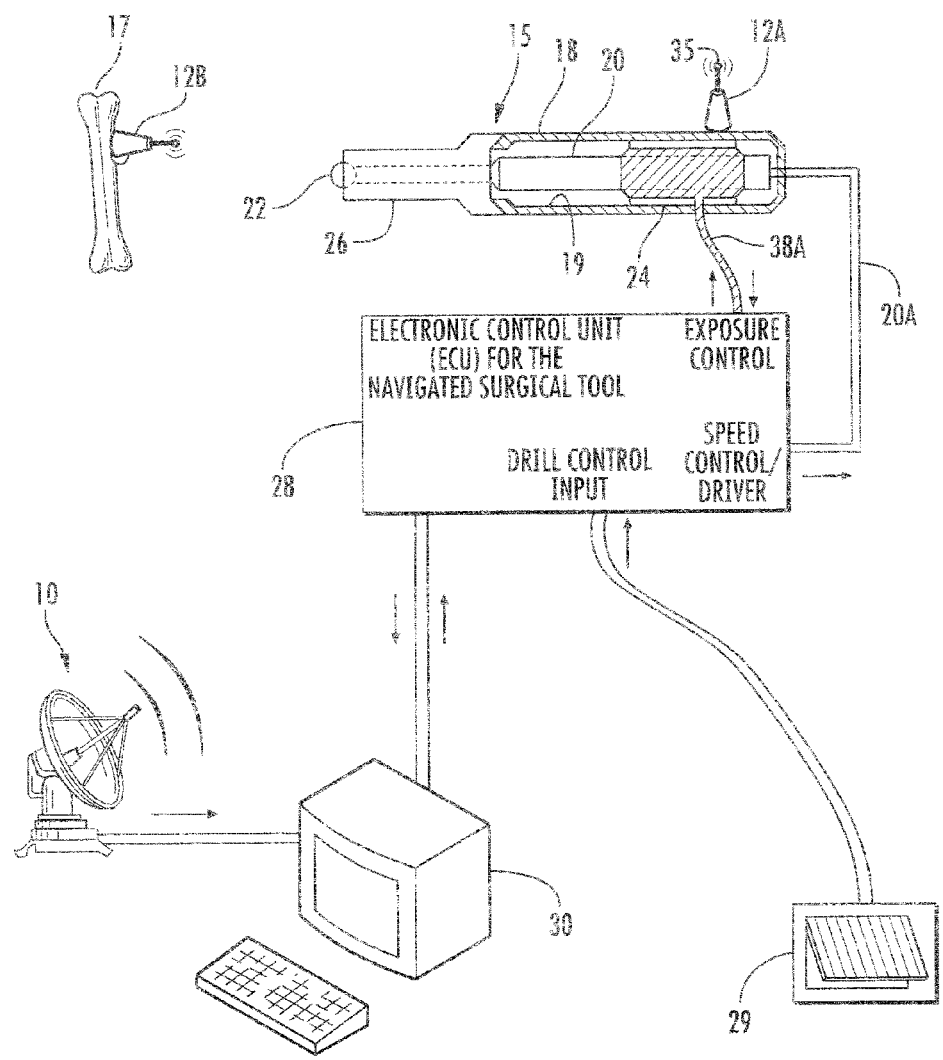
FIG. 2 is a functional diagram of an embodiment of a navigated surgical tool system configuration implementing various components of the navigated surgical tool kit in accordance with the present invention.

FIG. 2 shows an exemplary surgical layout implementing various components of the navigated surgical tool kit according to one embodiment of the present invention. The tool kit preferably includes a handpiece 15, a guard 26, a drill 20 with an end effector 22, an electronic control unit (ECU) 28, and a software application programming interface (API) that may be hosted, and executable on a computer 30. The control unit 28 may be connected to the computer 30 and may control drill 20 speed and/or exposure of the end effector 22. It is noted here that FIG. 2 is illustrative in nature, is not necessarily drawn to scale, and need not necessarily be construed as representing all the surgical tools that could be used in a navigated surgery in accordance with at least one embodiment of the invention.

The handpiece 15 may have an outer housing 18 and an inner housing 19 that receives at least a portion of the drill 20. The handpiece 15 may be configured to function as a robotically controlled shuttle that accepts and supports the user-supplied surgical drill 20 configured to be supported by the handpiece 15. The end effector 22 may be a rotating bur or other cutting member to cut the bone to a desired geometry and further acts as the primary motive drive generally to cut the patient anatomy. The drill 20 may thus be mechanically configured to couple to a drill-moving assembly 24 via guard attachment mechanism 50 disposed in the inner housing 19 of the handpiece 15.

A modular guard 26 also may be mounted on the drill 20 to control exposure of the end effector 22. The outer housing 18 may include a locking mechanism 50 such as a snap lock, threads, a snap-and-twist joint, etc. for easy attachment and detachment of the modular guard 26. The guard 26 is designed to shield the action of the end effector 22 of the drill 20 when the handpiece 15 of the navigated surgical tool 20 is in a "retracted" state. The guard 26 can be symmetric or asymmetric, but it is preferable to have the opening of the guard 26 lie near the central axis X-X of the drill 20 when the guard 26 is mounted on the handpiece 15. The optional guard 26 may preferably be provided with a guard attachment mechanism 50, as shown in FIGS. 3-12, as part of the tool kit to allow the user/surgeon to employ their desired guard 26 that may comprise various shapes to suit the procedure. The handpiece 15 may further be constructed of rigid plastic and/or metal, for example, to support the tracker 12A and drill 20.

As can be seen in FIG. 5, a user may select the drill 20 from a number of drills having an engagement portion 21 compatible with the handpiece 15. Engagement portion 21 may be a collar with extensions, threads, or other suitable configurations as described herein for engaging a retaining member 36 within the inner housing 19. Accordingly, the drill 20 may be easily attached to the handpiece 15 within the inner housing 19 by the user/surgeon such that the handpiece 15 provides semi-robotic functionality for a standard drill 20. In one embodiment, the retaining member 36 such as, for example, a threaded aperture, quarter-turn snap lock mechanism.

The handpiece 15 may further include a drill-moving assembly 24 that may include an actuator 38 such as, for example a servomotor, solenoid, pneumatic drive, linear motor, etc. as shown in FIGS. 4-12. Once attached, the drill 20 can be moved relative to the outer handpiece housing 18 through action of the actuator 38. The operation of actuator 38 may be controlled by the tool control unit 28 as discussed below and actuator may thus provide a secondary motive drive to the end effector 22 in and out of guard 26. Accordingly, actuator 38 may provide force to move the drill 20 along an "exposure" axis relative to the outer housing 18 that may preferably be coincident with the central axis X-X.

The design of the outer housing 18 may include distal support 52 for the drill 20 as shown in FIG. 6 not having guard 26 attached thereto. Distal support 52 may thus minimizes wobble at the end effector 22 of the drill 20 relative to the housing 18 to help stabilize the tool 14 during the cutting action. Such stability is desirable in surgical procedures where accuracy of cut is an important factor in a successful operation.

In one embodiment, the design of the outer housing 18 may also include mounting features, such as threaded apertures (not shown) to receive mounting members 13 to accept the tracker 12A. Mounting members 13 may be, in one embodiment for example, thumbscrew received by apertures in outer housing 18. Other mounting arrangement and/or sensors may be implemented with the present invention in accordance with the same.

Figure 3:
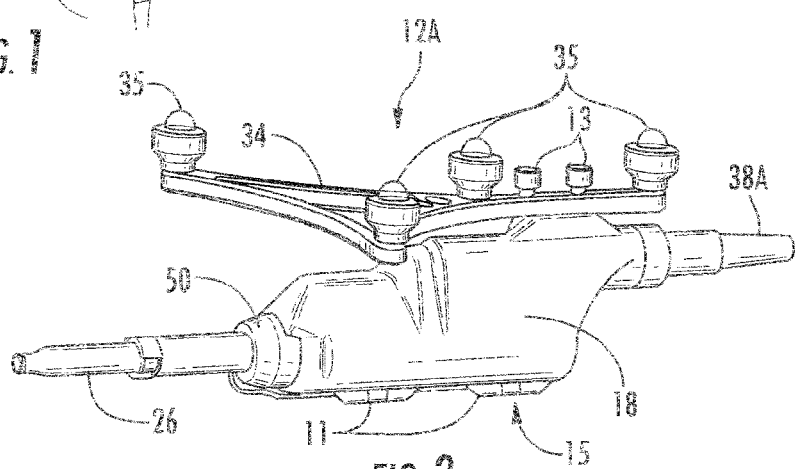
FIG. 3 is a perspective view of an embodiment of a handpiece in accordance with the present invention having an exemplary tracker attached thereto.

FIG. 3 illustrates the tracker 12A, with tracker frame 34 and markers 35 rigidly attached to a rigid object 14 to be tracked such as handpiece 15, for example. Markers 35 may be removable and replaceable if desired. The tracking of the handpiece 15 thus allows the navigation system to know the position of the end effector 22 of the drill 20 when the drill 20 is inserted into the handpiece 15. The tracker frame 34 may be large in size relative to the actual tracked end effector 22 of the drill 20. A similar tracker 12B also may be mounted on the bone 17 being operated on as shown in FIG. 2. Display software may be used to project the geometry of the tracked object 14, such as, for example, the drill 20 having handpiece 15 thereon, on the display screen 16 so that a virtual, real-time image of the object 14 and the surrounding anatomy of the patient bone 17 can be made available to the user/surgeon to aid in the surgery. A virtual interface 16 may depict the tracked tool 20 within the handpiece 15 in geometrical relationship with the tracked anatomy 17 of a patient. This interface 16 may remain visible to the user/surgeon during a surgical procedure. It is understood that multiple objects can be tracked, including rigid patient anatomy, such as the bone 17, in the same workspace with the same camera 10. However, each tracked object or part of a patient's anatomy must have its own tracker frame/array and the configuration of the markers must be unique for each object so as to enable the software, or any other computer processor analyzing image data, to distinguish between objects based on their respective trackers.

Figure 4:
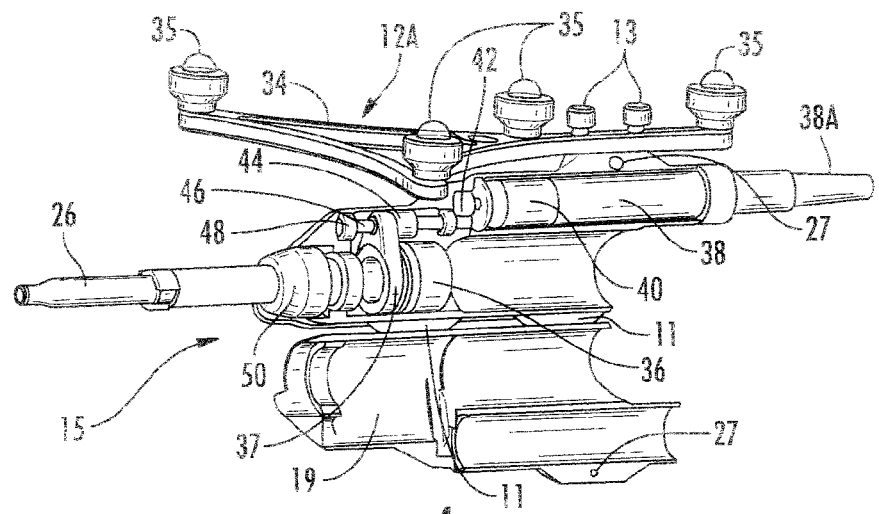
FIG. 4 is a perspective view of FIG. 3 having the handpiece in an opened position in accordance with the present invention.

FIG. 4 shows the inner constructional details of the handpiece 15 being openable via one or more hinges 11. The one or more hinges 11 thus allow access to the handpiece 15 inner housing 19 for adjustments, repair, etc. for example.

As mentioned above, the inner housing 19 of the handpiece 15 may also include the drill-moving assembly 24. In one embodiment, the drill-moving assembly may include an actuator 38, gearhead 40, gears 42, a lead screw nut 44, a lead screw/ball screw 46 and bearings 48 mounted on both ends of the lead screw 46. Accordingly as can be seen in FIGS. 4-12, and described in greater detail below, the handpiece 15 may receive at least a portion of the user-selected drill 20 for controlling the generally standard OEM drill 20 and moving the same with respect to the handpiece 15.

A guard attachment mechanism 50 may further be provided with the handpiece 15 to allow attachment of a cylindrical guard 26 to the attachment mechanism 50 for providing a shield to control the end effector 22. As can be seen in FIG. 5, the guard 26 may thus be attached to the attachment mechanism 50 while the inner housing 19 of the handpiece 15 may receive at least a portion of the drill 20 and may be mounted therein generally along the central axis X-X. Accordingly, various modular guards 26 may be implemented according to the desired user/surgeon preference.

FIG. 6 illustrates a close-up perspective view of the handpiece 15 without the guard 26 attached, leaving guard receiving recess 51 exposed within attachment mechanism 50. Accordingly, drill 20 has been mounted via retaining member 36 as the end effector 22 protrudes out of distal support 52 of the handpiece 15. The end effector 22 is thus stabilized by distal support 52 of the handpiece 15 as the casing about the shaft of the end effector 22 is adjacent distal support 52.

FIG. 7 shows a side view of an opened handpiece 15 with the tracker 12A attached thereto with mounting members 13 and the drill 20 inserted in a partially extended position therein. Accordingly, nut 44 on leadscrew 26 may be translated along leadscrew 26 about mid-way, causing end effector 22 of drill 20 to partially protrude from guard 26. Various other parts of the handpiece 15 discussed earlier hereinbefore are also identified in FIG. 7. Generally, with respect to the handpiece 15 figures, it is understood that similar parts depicted in different figures may be identified with similar reference numerals and may be attributed with similar functionality.

Figure 8:
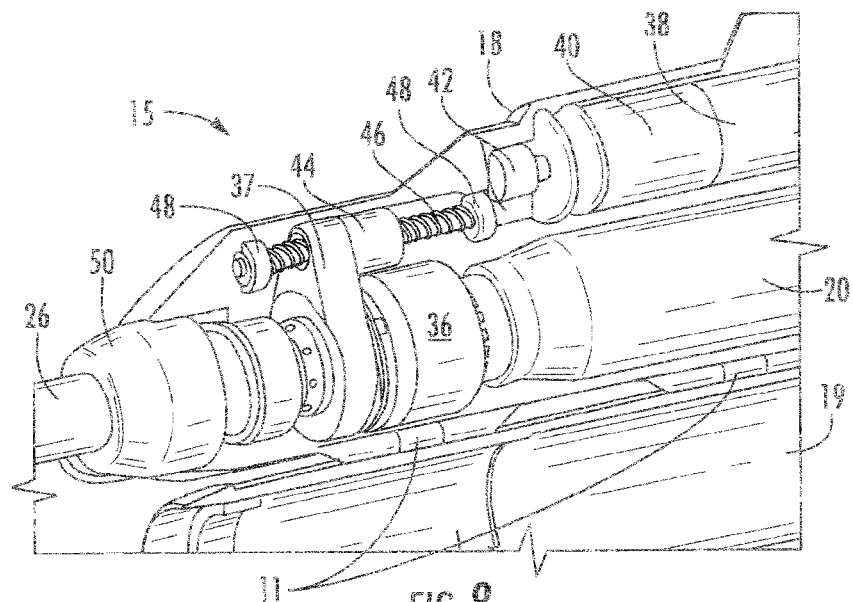
FIG. 8 is a partial close-up perspective view of FIG. 7 in accordance with the present invention.
Figure 12:
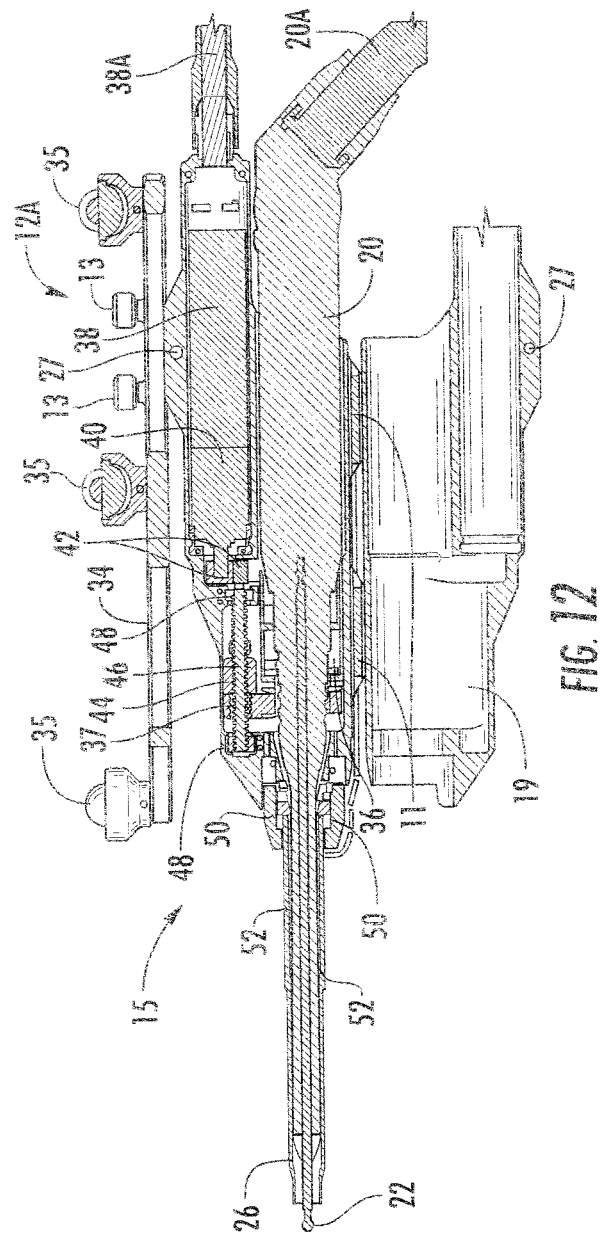
FIG. 12 is a cross-sectional view of FIG. 7 taken along a central axis X-X in accordance with the present invention.

FIG. 8 is another close-up view of the actuator 38 in communication with gear head 40, gears 42, lead screw 46, and other elements constituting the drill-moving assembly 24. Accordingly, as actuator 38 is supplied with signals and/or power, gearhead 40 may then rotate gears 42 such that lead screw 46 rotates. As lead screw 46 rotates, nut 44 travels along the lead screw 46. Nut 44 may further be attached to retaining member carriage 37, which is attached to retaining member 36. As shown in FIG. 8, the carriage 37 may be translated about ⅔rds along lead screw 46 to project at least a portion of end effector 22 out of guard 26 as can be seen in FIG. 12. As discussed herein, the drill 20 may be physically moved inside the inner housing 19 of the handpiece 15 to maintain exposure control of the end effector 22.

Figure 9:
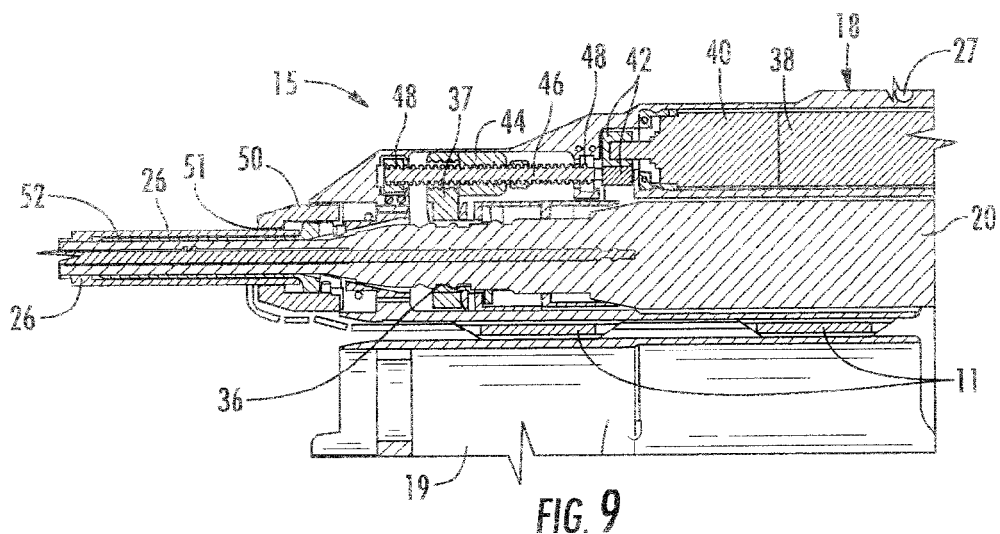
FIG. 9 is a partial cross-sectional view of FIG. 7 taken vertically along a central axis X-X in accordance with the present invention.

FIGS. 9 and 12 illustrate a cross-sectional views of the handpiece 15 having the drill 20 mounted therein via engagement mechanism 21 connected to receiving member 36 of the handpiece 15. Drill 20 may preferably be aligned along a central axis X-X such that end effector 22, positioned at the end of the drill shaft, may be protruded from guard 26 when the retaining member carriage 37 is translated toward the guard 26. FIG. 9 shows a close up of the guard 26 that may be slid over the end effector 22 and over distal support 52 into guard receiving recess 51 of the attachment mechanism 50. Accordingly, there may be a slight gap illustrated in FIG. 9 between the end of the distal support 52 and inside of the transition of the guard 26 while connected to the attachment mechanism 50.

Figure 10:
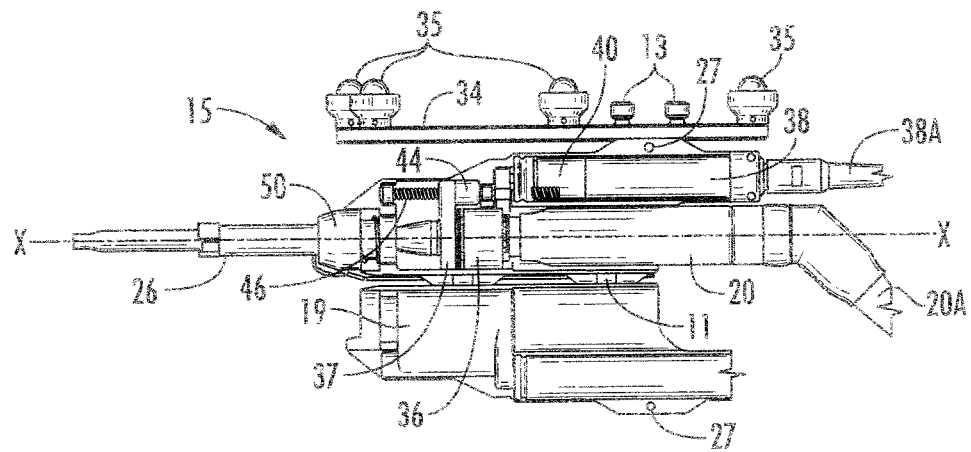
FIG. 10 is a plan view of an embodiment of a handpiece in an opened position and having an exemplary tool positioned therein in a retracted position in accordance with the present invention.
Figure 11:
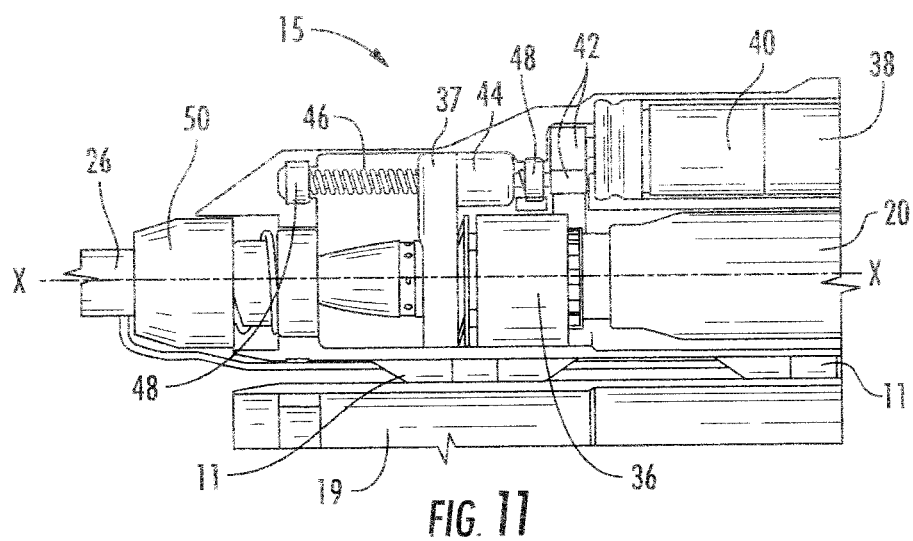
FIG. 11 a partial close-up plan view of FIG. 10 in accordance with the present invention.

FIG. 10 illustrates drill 20 retained within inner housing 19, except that the end effector 22 is in a retracted position wherein end effector 22 is not visible. Accordingly, retaining member carriage 37 is positioned close to actuator 38 and toward the rear opening of the handpiece 15.

As mentioned before, the exposure control (via ECU 28 shown in FIG. 2) of the end effector 22 may be necessary to prevent overcutting or erroneous cutting of the bone 17. When a bur retraction is desired to prevent damage to the bone 17, the exposure control module (not shown) in the ECU 28 may provide an appropriate signal to the actuator 38, which, in turn, may rotate the lead screw 46 via rotation of the gears 42. Thus, the rotating lead screw 46 axially moves the nut 44 towards the rear end of the housing 19, thereby also moving the drill 20 and end effector 26, which is mechanically coupled to the nut 44 via the attached retaining member 36. Thus, forward and backward motions of the end effector 22 can be obtained through appropriate rotation of the lead screw 46 by the actuator 38.

In accordance with at least one embodiment of the invention, the design of the outer housing 18 may further include suitable strain relief for the communication and driver cables that attach to the electronic control unit (ECU) 28. Exemplary cables/connections are shown in FIGS. 7, 10, and 12. The control unit 28 may contain electronic circuitry for signal control, amplification, and filtering, as well as communications and safety-related circuits.

In accordance with at least one embodiment of the invention, and as shown in FIGS. 2 and 7, signal and driver electrical lines that run from the handpiece 15 to the electronic control unit 28 can include: one signal cable 20A attached to the drill 20 for drill speed control; and a second cable 38A attached to the actuator 38. The cable 38A contains leads for power and positional feedback signals. The electronic control unit 28 provides those signals to the cable 38A from an included power control module (not shown). This power control module accepts positional commands from computer 30, which may communicate to the control unit 28 via a communication protocol (e.g., a USB [universal serial bus]-based signal communication). The power control module may then translate these commands to suitable voltages to be provided as driver signals to the actuator 38. The linear advancement of the drill 20 (i.e., the exposure of the end effector 22 relative to the bone 17 being cut) can be thus controlled by suitable modulation of the driver signals to the actuator 38.

In accordance with at least one embodiment of the invention, the ECU 28 may further include or encompass a microprocessor or microcontroller (not shown) that performs various tasks such as, for example, checking of consistency of data (e.g., data received from various data input sources such as the actuator 38), communications with devices attached to the ECU 28, interpretation of data received from various sensors (e.g., data received from the tracking system 10 via the computer 30, or feedback signals received from the actuator 38), and providing feedback and "watchdog" functionality to the overall operation of the drill-containing handpiece 15. In one embodiment, the ECU 28 also includes control circuitry that modulates the speed of the attached surgical drill by taking, as input, a signal from an operator-controlled foot pedal (or trigger) 29 and, in comparison to the commands given by the computer 30, by providing a modified speed signal to the drill 20 (via cable 20A). This modified speed signal thus allows an extra layer of safety and control of bone cutting by controlling the cutting rate of the drill in a reasonably conservative manner based on the feedback signals received (by the ECU 28) from the computer 30 in response to the tracking data obtained from the tracking system 10 (which tracks the relative position of the drill burr 22 with respect to the bone 17).

In addition to the drill-less handpiece 15 and the ECU 28, the surgical tool kit, according to one embodiment of the present invention, also includes a software API to allow a manufacturer (e.g., a third-party manufacturer) to integrate the handpiece 15 with a surgical navigation system. Thus, the handpiece 15 (when inserted with an appropriate drill) can be used as a navigated surgical tool in conjunction with a surgical navigation system. Such an API is schematically illustrated, by way of non-restrictive example, in FIG. 13.

Figure 13:
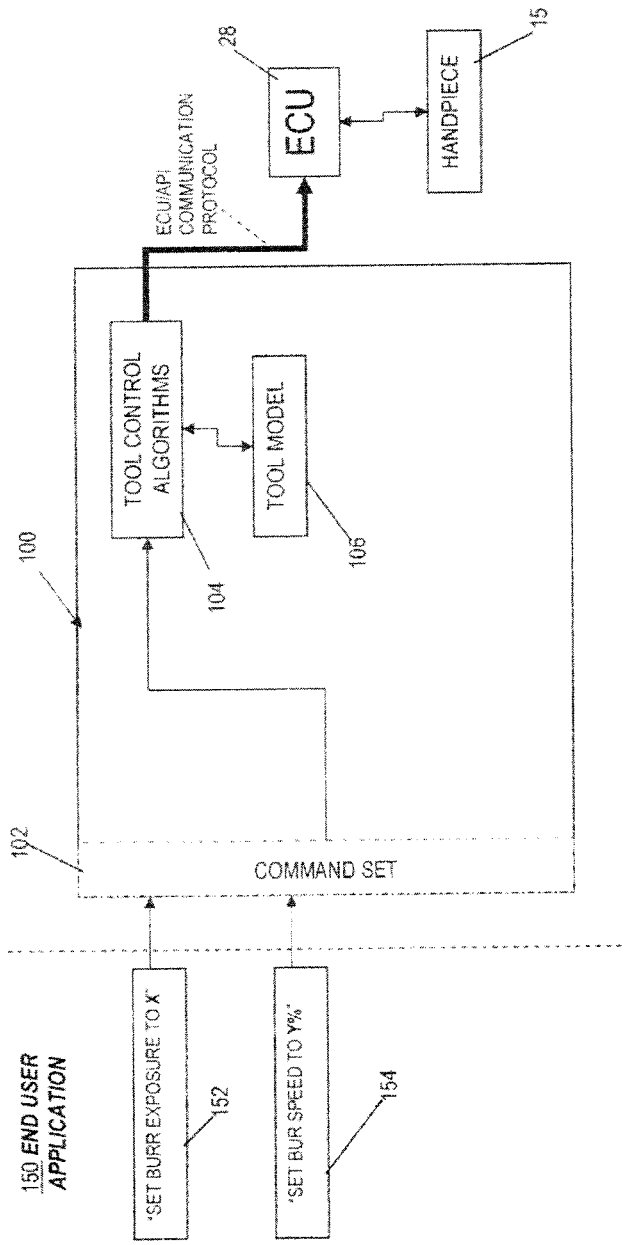
FIG. 13 schematically illustrates an embodiment of an application programming interface and associated components in accordance with the present invention.

In accordance with at least one embodiment of the invention, and as shown in FIG. 13, the API 100 can include a tool model 106 as well as a tool control module 104. During surgery, the API 100 can implement a command set 102 to directly command the handpiece 15 (e.g., via commands provided by an end user application 150 at a host computer, such as "go to exposure position X" [152] and "set burr speed to Y %" [154], etc.).

Figure 14:
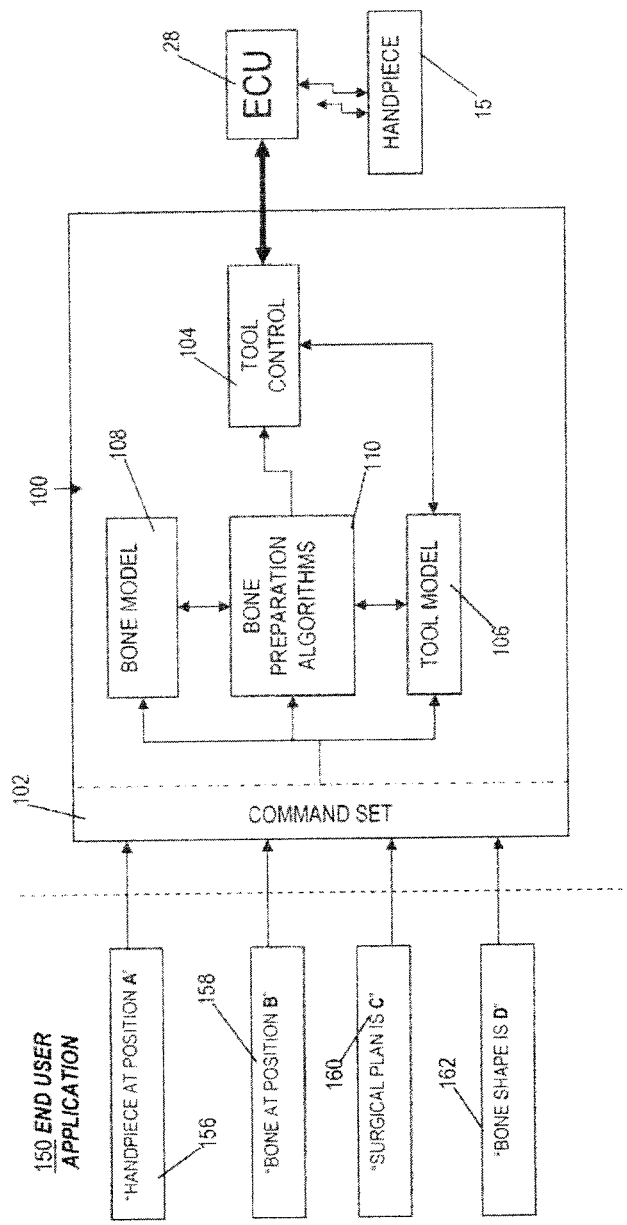
FIG. 14 schematically illustrates an embodiment of an application programming interface and associated components in accordance with the present invention.

In accordance with at least one embodiment of the invention, and as illustrated by way of non-restrictive example in FIG. 14, API 100 can also include a bone model 108 and bone preparation algorithms 110. The bone model 108 can accept as input, from an end user application 150, a software model pertaining to bone information (such as shape information 162) while bone preparation algorithms 110 can accept as input a surgical plan 160 and intra-operative position information (such as relative positions of the handpiece 15 [156] and the bone 17 to be cut [158], as well as the shape of the bone [162]). The bone model 108 and bone preparation algorithms 110, in conjunction with tool model 106 and tool control 104, can provide real-time control of the handpiece 15 by communicating with the ECU 28. The elements shown in FIGS. 13 and 14 may be utilized together. Any of a wide variety of specific methods and systems can be employed to control a shaping tool (such as the handpiece 15 when fitted with a drill), such as those disclosed in U.S. Pat. No. 6,757,582, supra.

In accordance with at least one embodiment of the invention, the API 100 may be installed on a host computer (e.g., the computer 30 in FIG. 2), and, merely by way of example, can be provided via a disc (e.g., a CD, a DVD, a floppy diskette, or any other data storage medium) or via a software download. In one embodiment, the API 100 provides a list of supported commands through which an existing computer program hosted on computer 30 can communicate with a shaping tool (e.g., the handpiece 15). Such commands can act to affect computation or data storage both within the host computer 30 and with respect to the ECU microcontroller 28 (which, e.g., itself may be provided with its own software pre-installed therein by a surgical tool kit supplier). In one embodiment, this ECU software may be changeable only by a separate firmware upgrade process. The ECU software may communicate with the host computer 30 by a communication protocol implemented by both the ECU software and the API 100. The communication protocol, in a preferred embodiment, is supported by a high-speed USB connection.

Figure 15:
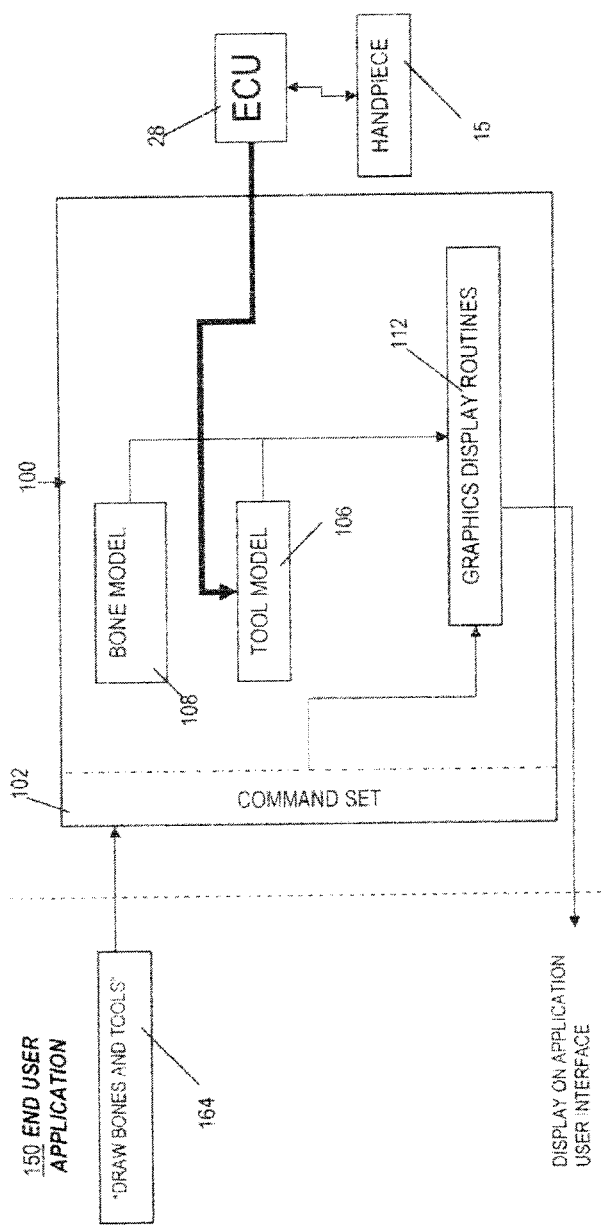
FIG. 15 schematically illustrates an embodiment of an application programming interface and associated components in accordance with the present invention.

In accordance with at least one embodiment of the invention, as schematically illustrated in FIG. 15, the API 100 can be configured to provide a user interface display (e.g., on the monitor of the computer 30 [see FIGS. 2 and 7] or on any other dedicated display screen) so that the surgeon can see an augmented view of the cutting action and intra-operative bone models during the surgery. These interface elements can be incorporated with navigation software, thereby allowing easy integration of the components of a surgical tool kit (e.g., comprising the handpiece 15, the ECU 28, and the API 100) with the user's choice of surgical navigation system. Accordingly, graphics display routines 112 can be included in API 100 to be in communication with the bone model 108 and tool model 106, while receiving a command (102) based on a prompt or input from end user application 150, e.g., to "draw bones and tools" (164). The elements shown in FIGS. 13, 14 and 15 may be utilized together.

From the foregoing, it can be appreciated that a navigated surgical tool kit, in accordance with at least one embodiment of the present invention, provides a surgeon (or hospital) a great degree of flexibility in implementing a navigated surgical system. The handpiece 15 of the kit provides a housing (equipped with suitable drill motion control and tracking attachments) to receive a surgeon's drill 20 to form a navigated surgical tool that the surgeon can use in a freehand manner, while providing an added layer of safety (under the control of the electronic control unit of the tool kit) that ensures a precise and accurate cut. Thus, the handpiece 15, when inserted with an appropriately configured drill 20, can be used as a navigated surgical tool in a surgical navigation system, such as a navigation system of a third party.

As such, it can further be appreciated that a software API of a tool kit, in accordance with at least one embodiment of the invention, provides a visual interface 16 of patient anatomy as well as navigation information (e.g., relating to object 14 location and orientation) to guide the surgeon during a surgical procedure. These interface elements can be incorporated with existing navigation software, thereby allowing easy integration of the components of a present surgical tool kit (i.e., the handpiece 15, the electronic control unit, and the API) with the user's (e.g., surgeon's) choice of surgical navigation system. Thus, a navigated surgical tool is provided that can accommodate a wide variety of user-selected surgical drills and tracking systems and can also operate with third-party navigation software, thereby giving the user (e.g., a surgeon or a hospital) more flexibility in implementing a navigated surgical system.

Figure 16:
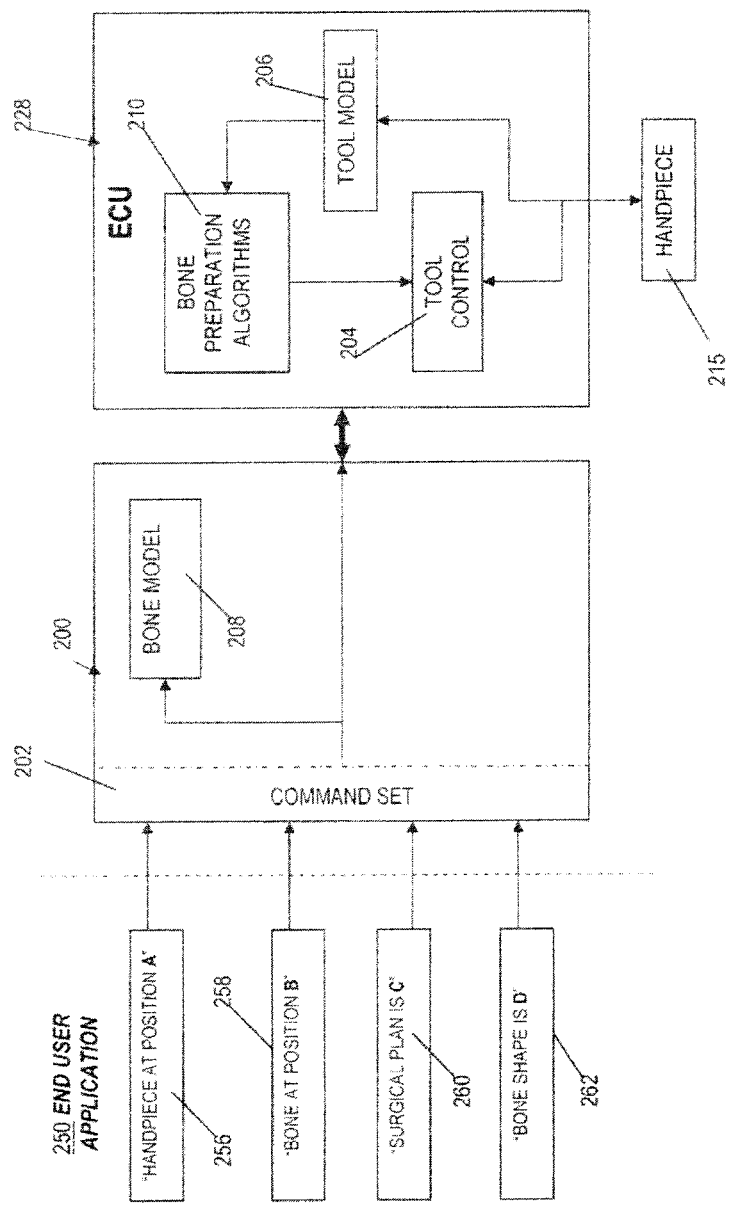
FIG. 16 schematically illustrates an embodiment of an arrangement of an application programming interface and electronic control unit in accordance with the present invention.

In accordance with at least one variant embodiment of the invention, as shown in FIG. 16, various modules and/or functions and/or elements can be split between an API 200 and an ECU 228. Conceivably, any or all of the elements described with respect to FIGS. 13-15 as being resident in or associated with an API can be hosted in or associated with ECU 228. FIG. 16 provides but one illustrative and non-restrictive example of this possibility. Thus, as shown API 200 can accept as input a command set 202 based on prompts or input from an end user application 250, such as "handpiece at position A" (256), "bone at position B" (258), "surgical plan is C" (260) and "bone shape is D" (262). While bone model 208 may be hosted in or associated with API 200, other elements such as a tool control module 204, a tool model 206 and bone preparation algorithms 210, can be hosted in or associated with ECU 228, whereupon these elements are in communication with a handpiece 215.

Although the invention has been described in detail for the purpose of illustration based on what is currently considered to be the most practical and preferred embodiment(s), it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. Since other modifications and changes varied to fit particular operating requirements and environments will be apparent to those skilled in the art, the invention is not considered limited to the example chosen for purposes of disclosure, and covers all changes and modifications which do not constitute departures from the spirit and scope of this invention.

What is claimed is:

1. A handpiece arrangement for a tool, the handpiece arrangement comprising:
   a retaining member configured to receive at least a portion of the tool in a secure position;
   a guard configured to cover at least a portion of an end effector portion of the tool; a tracker configured to indicate a position of the tool;
   at least one mounting member configured to receive the tracker to provide a tracking target for at least a portion of a tracking system;
   an actuator mounted to said handpiece and in communication with said retaining member, wherein said actuator is configured to move said retaining member with respect to said guard to control exposure of said end effector in response to signals received from the tracking system.

2. The handpiece arrangement of claim 1, wherein the tool is configured to provide a primary motive drive to move an end effector of the tool and said actuator is configured to provide a secondary motive drive to move the end effector in another modality than said primary motive drive motion.

3. The handpiece arrangement of claim 1, wherein said handpiece further comprises a tracker configured to indicate the location of the tool.

4. The handpiece arrangement of claim 1, wherein said handpiece further comprises an attachment mechanism configured to releasably secure said guard.

5. The handpiece arrangement of claim 1, wherein said retaining member is further configured to releasably secure at least a portion of the tool within said handpiece.

6. The handpiece arrangement of claim 1, wherein said handpiece further comprises a support extending away from said retaining member for supporting at least a portion of the tool.

7. A navigational surgical tool, comprising:
an end effector configured to shape an object;
a tracker configured to indicate a position of said end effector;
a handpiece including
 a first attachment portion configured to retain at least a portion of the tool in a secure position;
 a second attachment portion configured to retain said tracker;
 a guard configured to cover at least a portion of the end effector;
 an actuator mounted to said handpiece and in communication with said first attachment portion, wherein said actuator is configured to move said first attachment portion with respect to said guard to control exposure of said end effector.

8. The navigated surgical tool of claim 7, further comprising a third attachment portion configured to releasably receive the guard.

9. A navigational surgical tool system, comprising:
a surgical tool;
a tracking system configured to make a location of said tool known;
a handpiece configured to:
 receive at least a portion of said tool in a mechanically secure position relative to at least a first portion of said handpiece;
 receive, in a position fixed relative said handpiece, a portion of a tracking system;
 contain an actuator configured to move said tool relative to at least a second portion of said handpiece; and
a guard configured to cover at least a portion of said tool and mechanically coupled to said second portion of said handpiece wherein the actuator controls exposure of at least a portion of said tool relative to said guard.

10. An apparatus comprising:
a surgical shaping tool including an engagement portion and an end effector;
a guard configured to cover at least a portion of the surgical shaping tool;
a handpiece comprising:
 a retaining member configured to removably secure the engagement portion of the surgical shaping tool to a carriage member; a tracker frame including a plurality of markers rigidly affixed to the tracker frame, wherein the tracker frame is securely coupled to the handpiece;
 a guard attachment mechanism configured to removably receive the guard; and
 an actuator configured to translate the carriage member in a linear direction relative to the guard to control exposure of said end effector.

11. The apparatus of claim 10, wherein the handpiece includes a leadscrew coupled to the actuator, and wherein the carriage member translates on the leadscrew.

12. The apparatus of claim 10, wherein the actuator includes a solenoid configured to translate the carriage member.

13. The apparatus of claim 10, wherein the engagement portion includes a threaded portion configured to engage a mating threaded portion on the carriage member.

14. The apparatus of claim 10, further comprising a tracker frame including a plurality of markers rigidly affixed to the tracker frame, wherein the tracker frame is securely coupled to the handpiece.

15. The apparatus of claim 10, wherein the guard includes a tapered distal end terminating in a opening sized to receive a distal end of the end effector.

* * * * *

UNITED STATES PATENT AND TRADEMARK OFFICE
CERTIFICATE OF CORRECTION

PATENT NO.       : 8,961,536 B2
APPLICATION NO.  : 13/092851
DATED            : February 24, 2015
INVENTOR(S)      : Nikou et al.

It is certified that error appears in the above-identified patent and that said Letters Patent is hereby corrected as shown below:

In the Claims

In column 7, line 18, in Claim 7, after "including", insert --:--, therefor

Signed and Sealed this
Eighth Day of September, 2015

Michelle K. Lee
*Director of the United States Patent and Trademark Office*